United States Patent [19]

Lindsay et al.

[11] Patent Number: 4,828,693
[45] Date of Patent: May 9, 1989

[54] WATER PRESSURE REGULATOR FOR HEMODIALYSIS APPARATUS

[75] Inventors: Edward R. Lindsay, Clearwater; James D. Aid; Norman F. Cameron, both of St. Petersburg, all of Fla.

[73] Assignee: Baxter Travenol Laboratories, Inc., Deerfield, Ill.

[21] Appl. No.: 99,545

[22] Filed: Sep. 22, 1987

[51] Int. Cl.⁴ .............................................. B01D 21/30
[52] U.S. Cl. .................................... 210/137; 210/188; 210/195.2; 210/321.71
[58] Field of Search ...................... 210/90, 134, 321.71, 210/637, 646, 137, 188, 195.2

[56] References Cited

U.S. PATENT DOCUMENTS

| | | | |
|---|---|---|---|
| 3,598,727 | 8/1971 | Willcock | 210/321.71 |
| 3,878,095 | 4/1975 | Frasier et al. | 210/321.71 |
| 4,054,522 | 10/1977 | Pinkerton | 210/321.71 |
| 4,060,485 | 11/1977 | Eaton | 210/90 |
| 4,209,391 | 6/1980 | Lipps et al. | 210/929 |
| 4,477,342 | 10/1984 | Allan et al. | 210/321.71 |
| 4,715,959 | 12/1987 | Allan et al. | 210/321.71 |
| 4,718,022 | 1/1988 | Cochran | 210/321.71 |

*Primary Examiner*—Ernest G. Therkorn
*Assistant Examiner*—Coreen Y. Lee
*Attorney, Agent, or Firm*—Paul C. Flattery; Macdonald J. Wiggins; Charles R. Mattenson

[57] ABSTRACT

A pressure regulating system for a hemodialysis machine utilizes a deaeration pump and a regulator in a deaeration loop for minimizing pressure and flow transients in a heated water supply. The deaeration loop has the pump, a deaeration pressure regulator, a deaerator, and a back pressure regulator. The pump produces a negative pressure in heated water entering the deaeration pressure regulator to circulate the water in the deaeration loop and to enhance removal of air from the water. The back pressure regulator controls the loop water pressure to a value greater than the incoming water pressure and supplies water to the dialyzer system of the machine isolated from supply water pressure and flow variations.

6 Claims, 3 Drawing Sheets

WATER PRESSURE REGULATOR FOR HEMODIALYSIS APPARATUS

BACKGROUND OF THE INVENTION

1. Field of the Invention

The present invention relates to hemodialysis apparatus, and more particularly to a system for minimizing the effects of water pressure transients on the accuracy and consistency of patient dialysis.

2. Description of the Prior Art

Hemodialysis machines used to extract waste from human blood of patients having kidney failures or disorders utilize a dialyzer in which the blood flows through one chamber and a dialysate solution flows through another chamber separated from the first chamber by a membrane. The dialysate picks up metabolic waste products and ultrafiltrate from the blood passing through the dialyzer. In many such machines, incoming water is first treated externally to the machine to remove impurities, and thereafter pressure controlled, filtered, heated, and applied to a proportioning pump which is also connected to a supply of concentrated dialysis solution. The proportioning pump produces a carefully controlled dialysate solution from the water and concentrate. For example, a 34 parts water and 1 part dialysate concentrate is typical. The dialysate may be applied to a flow controller or other means which controls the rate of flow of the dialysate through the dialyzer.

To maintain the exact flow, pressure, and concentration of the dialysate through the system for consistent dialysis performance, it is necessary that the water flow and transients be minimized. Otherwise, such transients in the incoming water pressure will occur and will degrade the accuracy of the ultrafiltration control system. Although systems utilize pressure regulators to maintain the pressure, these regulators suffer from normal hysteresis and inertial effects which permit a drop or rise in pressure before correction can occur. Therefore, there is a need for a system which will maintain a constant pressure of water to the dialysate proportioning pump and flow controller when the input pressure and flow varies or experiences transients.

SUMMARY OF THE INVENTION

The present invention is a water system for supplying treated water to a dialysate proportioning pump which will maintain an essentially constant water pressure. Typical prior art systems utilize means for removing air entrapped in the incoming water from the water stream prior to the proportioning pump. The air is removed in a deaeration loop utilizing a deaerator having a float valve and air outlet. The incoming water is fed to a deaerator pressure regulator having an output to the deaerator. The deaerator output is connected to a pump, thence back to the pressure regulator completing the deaeration loop. The pump creates a negative pressure in the deaerator pressure regulator, drawing the incoming water into the deaerator at which point the entrapped air in the water escapes via the float valve and air outlet at a lower negative pressure. The deaeration pressure regulator controls the negative pressure to a selected value, for example; −23 inches of mercury. The incoming water to the deaeration pressure regulator is generally controlled by a first pressure regulator to 12 psig. The output water from the deaeration pressure regulator is supplied to the proportioning pump.

The invention utilizes the above described prior art system adding a second regulator, termed a back pressure regulator, to receive water from the deaeration pump and to control the pressure of that water to a value higher than 12 psig; for example, 15 psig. The output from the back pressure regulator then provides the water to the dialysate proportioning pump. As may now be recognized, the pressure of the water to the proportioning pump is now independent of the incoming water pressure since the deaerator loop serves as a constant volume source of water to the pump and the pump is independent of the incoming water pressure and flow. Thus, disturbances at the water input are effectively buffered and eliminated by the invention.

It is therefore a principal object of the invention to provide a water pressure and flow control system for a hemodialysis apparatus which will prevent source water pressure and flow transients and variations from affecting the ultrafiltration control system and dialyzer performance.

It is another object of the invention to provide a system having a back pressure regulator in the deaeration loop of a hemodialysis machine to supply water to the dialysate proportioning pump utilizing the deaeration pump and the back pressure regulator for providing water at a pressure independent of the source pressure.

It is still another object of the invention to provide a system in a hemodialysis apparatus utilizing a deaeration pump isolated from the primary water source of the machine to produce a constant pressure and flow of treated, heated, and deaerated water to the dialysate proportioning pump, dialyzer fluid circuit utilizing a back pressure regulator in the deaeration loop.

These and other objects and advantages of the invention will become apparent from the following detailed description when read in conjunction with the drawings.

DETAILED DESCRIPTION OF THE PREFERRED EMBODIMENT

Figure 1:
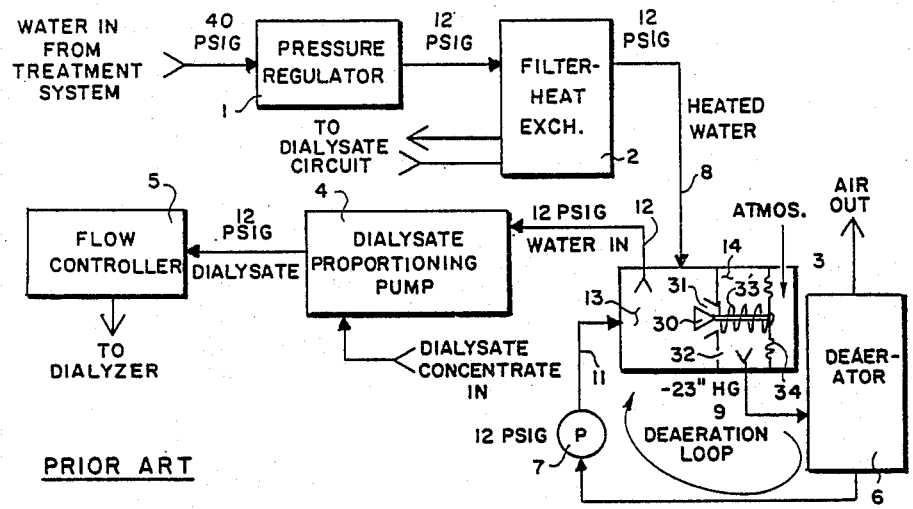
FIG. 1 is a simplified block diagram of a water system for a hemodialysis machine in the prior art.

FIG. 1 shows a simplified block diagram of the water and dialysate portion of a typical hemodialysis machine. For example, the model SPS-450 hemodialysis apparatus manufactured by Baxter, Inc. utilizes this system. Water is treated in a water treatment system and thereafter enters pressure regulator 1, nominally at 40 psig pressure. Typically, pressure regulator 1 controls the output pressure to 12 psig. The water is passed through a filter-heat exchanger unit 2 which heats the water to a predetermined temperature. The heated water is then sent via line 8 to a deaerator pressure regulator 3 shown in schematic form in FIG. 1.

As will be noted, deaerator pressure regulator 3 includes an input/output chamber 13 into which heated water flows from line 8. Deaerator pressure regulator 3 is a part of a deaeration loop which includes deaerator 6 and positive displacement gear deaerator pump 7. Water flowing into the deaeration loop from line 8 will normally contain air which must be removed to optimize dialyzer performance and measurement of ultrafiltration through the dialyzer in the hemodialysis apparatus. The deaerator 6 performs the air removal function. The function of the deaeration pressure regulator is to subject the incoming water to a negative pressure of about $-23$ inches of mercury by means of deaeration pump 7.

When the system is not in operation, it may be noted that spring 33 will force diaphragm 34 to the right, closing valve seat 31 with valve body 30. When deaeration pump 7 is operating, a $-23$ inches of mercury pressure occurs in chamber 33 moving diaphragm 34 to the left and opening regulator valve seat 31. Bleed orifice 32 permits an initial flow of water from chamber 13 into chamber 14 prior to the opening of valve 30, 31 to prevent excess pressure in chamber 13 from pump 7. When valve 30, 31 opens, the water from chamber 14 is drawn into the deaerator 6. Although not shown, deaerator 6 includes a float and float chamber at the upper end thereof and an air outlet valve controlled by the float. The negative pressure in the deaerator will cause the air in solution to expand, producing large bubbles of air which will float to the top and be expelled through the float air outlet valve to a low pressure part of the hemodialysis apparatus. The deaerated water is drawn from the lower end of deaerator 6 over line 10 to pump 7 via pump 7 and flows via line 11 back to chamber 13.

An output line 12 from chamber 13 is provided; however, pump 7 produces a flow rate in the deaeration loop which is considerably higher than the flow rate required by the dialyzer. For this reason, most of the water will circulate through the deaeration loop two or more times before leaving chamber 13 on line 12. Water which enters chamber 13 on line 8 at about 12 psig will then, due to continuity of flow, exit chamber 13 on line 12 at about 12 psig, neglecting slight pressure drops through the other elements of the system. The internal porting in chamber 13 is arranged to ensure that flow inline 8 will always enter valve 30, 31. Water flows out on line 12 and is routed to dialysate proportioning pump 4 or other proportioning system.

As is common, the dialysate is stored in concentrated form and must be diluted in an exact proportion with water prior to use as the dialysate for a dialyzer. For example, in the system shown in FIG. 1, a ratio of 34 parts of water to 1 part of dialysate concentrate is commonly used. The output from dialysate proportioning pump provides the proper dialysate solution for use by the dialyzer and its flow rate is controlled by flow controller 5 to a predetermined flow rate for the hemodialysis apparatus.

The prior art system of FIG. 1 operates efficiently in steady state conditions. However, in instances where the inlet water is subject to pressure transients, pressure regulator 1 and deaeration pressure regulator 3, which are mechanical in nature, cannot respond instantaneously to maintain the predetermined pressure; for example in this instance, 12 psig. Part of this problem results from the water treatment systems employed for dialysis which include softeners and reverse osmosis type treatment and, have limited capacity resulting in pressure transients on occasions. The many swings in inlet pressure will therefore be translated through the system to the flow controller 5 input. The Baxter hemodialysis machines utilize automatic flow control systems since the accurate operation of a dialyzer is dependent upon the relative flow rates in the apparatus. When transients occur at flow controller 5, in flow and out flow sensors will shift to a new operating point, introducing an error in their signals and thereby affect the accuracy of the ultrafiltration control system.

Another problem in such prior art systems results from operation of deaerator 6. As air comes out of solution in the deaeration loop, it collects at the top of deaerator 6. Normally, the air will exit continuously but, at times, it suddenly is purged from the deaerator 6. When this occurs, the void occupied by the air fills with water requiring a sudden inflow of water at the water inlet. Inlet pressure regulator 1 (FIG. 1) adjusts to maintain pressure and the usual proportional operating band of the regulator produces a shift in pressure that can be as great as 2 psig.

Figure 2:
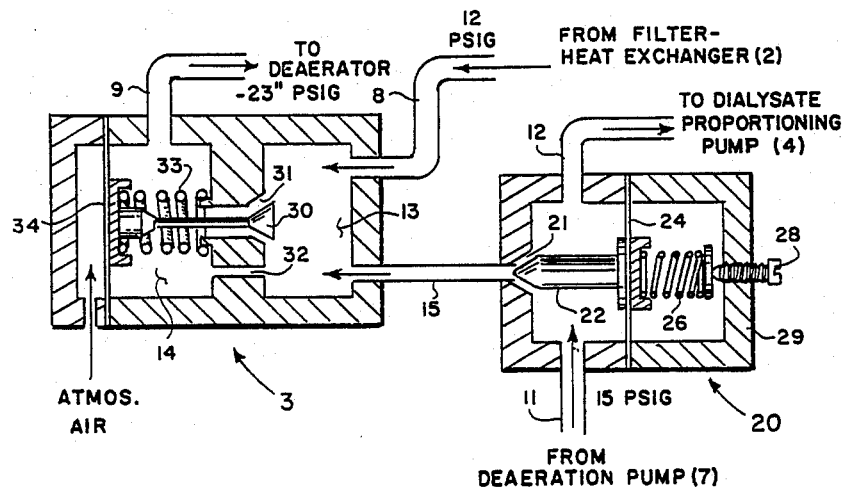
FIG. 2 is a cross-sectional view of a deaeration pressure regulator and a back pressure regulator used in the present invention.
Figure 3:
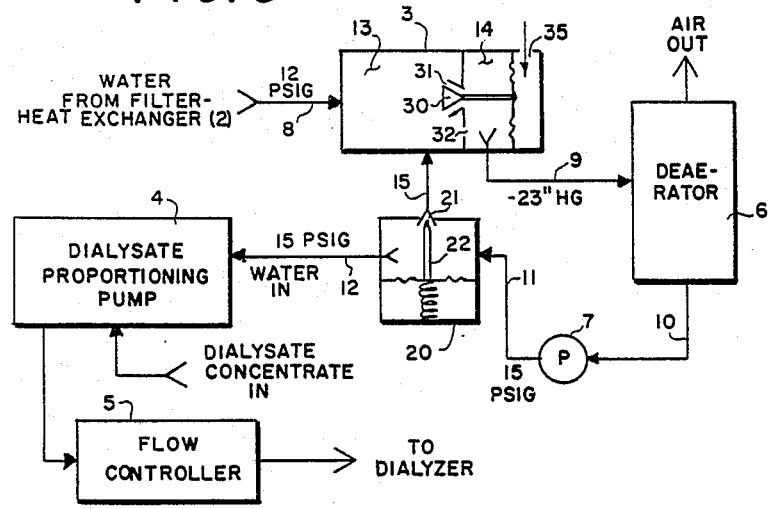
FIG. 3 is a simplified schematic diagram of the deaeration loop of the invention utilizing the devices shown in FIG. 2.

FIGS. 2 and 3 illustrate the improvement of the present invention which essentially eliminates the effects of input pressure transients on the accuracy of the dialysis operation in the hemodialysis apparatus. A back pressure regulator 20 shown in simplified cross-sectional view in FIG. 2, is added into the deaeration loop. Back pressure regulator 20 has a diaphragm 24, spring 26, and adjusting screw 28 which control the regulator needle 22 in conjunction with valve seat 21. Deaeration pump 7 is connected to an input to back pressure regulator 20 with the pressure controlled output line 15 connected to chamber 13 of aeration pressure regulator 3. Line 12, from back pressure regulator 20, which formerly connected to deaeration pressure regulator 3, now connects to back pressure regulator 20 as best seen from the simplified schematic diagram of FIG. 3.

Water from the filter heat exchanger 2 now enters chamber 13 via line 8 flowing through valve 30, 31 into chamber 14 and is drawn into the deaeration loop by the negative pressure on line 9. As will now be recognized, deaeration pump 7 can now be operated at a pressure higher than and independent of the 12 psig input pressure from line 8. Consequently, back pressure regulator 20 is adjusted to produce such higher pressure, for example, 15 psig pressure, in the deaeration loop and on line 12 to dialysate proportioning pump 4. Thus, the water pressure to flow controller 5 is now independent of the incoming water pressure and therefore the transients in that pressure will not reflect through to flow controller 5.

The system will operate as in the prior art system of FIG. 1 on startup. Back pressure regulator 20 will be closed as will control valve 30, 31 of the deaeration pressure regulator 3. When operation of the system is initiated, pressure from line 18 will permit water through bleed hole 32 into chamber 14 and pump 7 will cause back pressure regulator to operate at the adjusted pressure point. When the negative pressure in chamber 14 occurs, valve 30, 31 will open as previously discussed, enabling the deaeration process.

ALTERNATIVE EMBODIMENT

Figure 4:
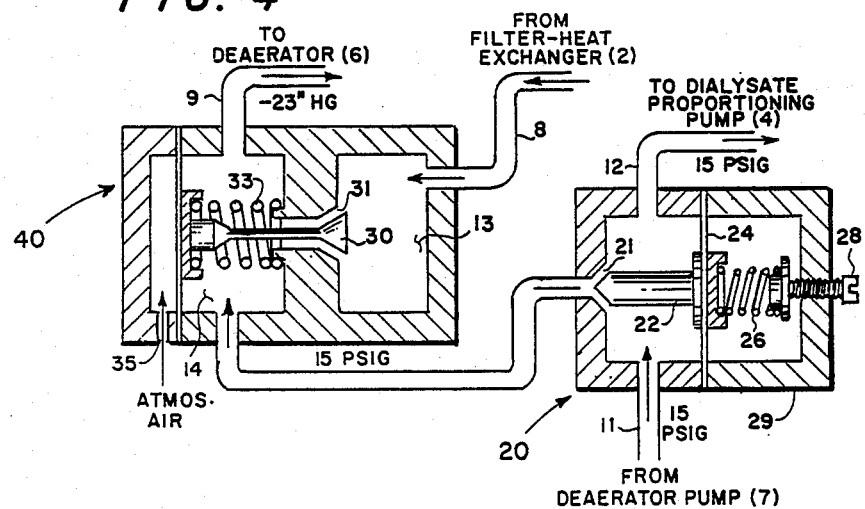
FIG. 4 is a cross-sectional view of a modified deaeration pressure regulator and a back pressure regulator in accordance with an alternative embodiment of the invention.
Figure 5:
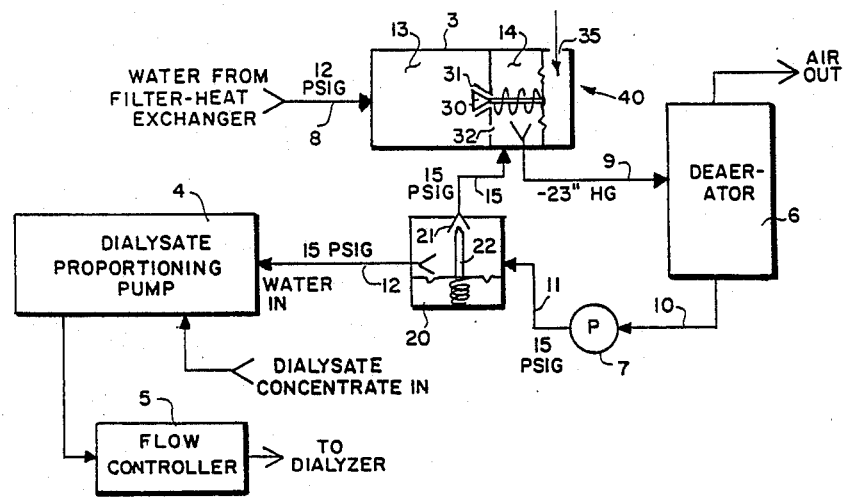
FIG. 5 is a simplified schematic diagram of the alternative embodiment of the invention utilizing the elements shown in FIG. 4.

Turning now to FIGS. 4 and 5, an alternative embodiment of the invention is shown. A modified deaeration pressure regulator 40 is utilized having a single port into chamber 13 connected by line 8 to filter heat exchanger 2. Line 15, which in the first embodiment connected to chamber 13, now connects to chamber 14. The remainder of the deaeration loop connections remain the same as shown in FIG. 5 with the output from back pressure regulator 20 being connected to dialysate proportioning pump 4. The advantage of this implementation is that the pressure regulator 1 of FIG. 1 and related control solenoids (not shown) can be eliminated and the source pressure applied to chamber 13. On startup, valve 30, 31 will be closed and chamber 13 can easily handle the source pressure which would rarely exceed 100 psig. The deaeration pump 7 will produce the required negative pressure in chamber 14 opening valve 30, 31 as required.

As in the first embodiment, water is supplied to dialysate proportioning pump via lines 12 directly from the deaeration loop with the pressure controlled by pump 7, ensuring isolation from pressure transients in the water supply system.

The deaeration pump 7, as mentioned above, produces a greater flow than required by the dialyzer in the hemodialysis apparatus described. For example, the dialyzer may utilize a flow in the range of 300–500 ml/min while the pump 7 may produce flows in the range of 1.5–2 l/min.

Figure 6:
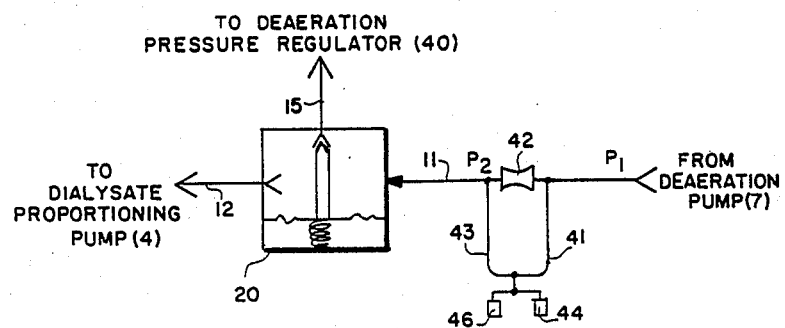
FIG. 6 is a schematic diagram of a portion of the deaeration loop showing a means for obtaining water flow for rinsing of fluid circuits in a hemodialysis apparatus.

Referring now to FIG. 6, a source of warm, deaerated water is periodically needed at rinse ports 44 and 46 for rinsing the proportioning pump concentrate lines and during system disinfection.

The arrangement of FIG. 6 shows schematically the use of deaeration pump 7 to provide rinse water to ports 44 and 46. A flow restrictor 42 is inserted in line 11 between pump 7 and back pressure regulator 20. Rinse ports 44 and 46 are each required to provide a source of warm deaerated water at a flow of about 15 ml/min. Lines 41 and 43, which may be small tubing, are connected across flow restrictor 42. A pressure drop of about 4 psig across rinse restrictor 42 will produce the required flow through lines 41 and 43 without interfering with the normal deaeration loop operation.

Normally closed ports 44 and 46 are connected to line 41 and may be temporarily connected to portions of the machine for rinsing by one or two rinse lines having a connector that opens port 44 or 46 when connected thereto. Continuous flows at all times through the loop formed by lines 41 and 43 independently of the rinse ports assures that no stagnation can occur and that proper rinsing will take place during disinfection cycles.

Although specific systems of the invention have been disclosed, these are for exemplary purposes only and various modifications can be made thereto without departing from the spirit and scope of the invention.

We claim:

1. In a hemodialysis apparatus having means for supplying heated water under pressure in which said water is subject to pressure and flow transients, a deaeration and pressure regulating system isolated from said pressure transients, comprising:
   (a) deaeration pressure regulating means connected to receive said heated water for regulating a negative pressure of said heated water;
   (b) deaeration means having an input connected to said deaeration pressure regulator to receive said heated water under negative pressure for removing air therefrom, and an outlet for deaerated water;
   (c) pump means, having an input connected to said outlet to receive deaerated water from said deaeration means, for producing said negative pressure; and
   (d) back pressure regulating means having
      (i) a housing having an inlet connected to said output of said pump means, an outlet connected to said deaeration pressure regulating means, and an outlet connected to supply a flow of said heated deaerated water to said hemodialysis apparatus at a first flow rate,
      (ii) a valve seat and valve, said valve operatively connected to a diaphragm in said housing; and
      (iii) biasing and adjustment means operatively connected to said diaphragm for adjusting said pressure of said circulating heated water, said back pressure regulating means connected to an output of said pump means and to said deaeration pressure regulating means, whereby said deaeration pressure regulator means, said deaeration means, said pump means and said back pressure means form a deaeration loop, said back pressure means for controlling the pressure of said heated water circulating in said deaeration loop independently of the regulated pressure of said water from said source, said back pressure regulating means having an output for providing said hemodialysis apparatus with heated deaerated water at a constant pressure.

2. The apparatus as recited in claim 1 in which said deaeration pressure regulating means includes:
   a first chamber having a first input connected to said heated water supplying means and a second input connected to said back pressure regulating means;
   a second chamber adjacent said first chamber having an output connected to said input of said deaeration means; and
   a pressure regulating valve disposed between said first and second chambers, said valve biased to a closed position when said deaeration pump is non-operative and to an open position responsive to said negative pressure.

3. The apparatus as recited in claim 2 in which said first and second chambers include a bleed orifice therebetween.

4. The apparatus as recited in claim 1 in which said deaeration pressure regulating means includes:
   a first chamber having an input connected to said heated water supplying means;
   a second chamber adjacent said first chamber having an output connected to said input of said deaeration means and an input connected to said back pressure regulating means; and
   a pressure regulating valve disposed between said first and second chambers, said valve biased to a closed position when said deaeration pump is non-operative and to an open position responsive to said negative pressure.

5. The apparatus as recited in claim 1 in which said pump means is a positive displacement gear pump.

6. The apparatus as recited in claim 1 which further includes:
   a flow restrictor disposed between said housing inlet and said pump output;
   a rinse line connected across said flow restrictor to form a flow of heated deaerated water at a second flow rate much smaller than said first flow rate around said restrictor; and
   at least one rinse port connected to said rinse line.

* * * * *